United States Patent
Zierke et al.

(10) Patent No.: US 8,586,750 B2
(45) Date of Patent: *Nov. 19, 2013

(54) METHOD FOR THE PRODUCTION OF HALOGEN-SUBSTITUTED 2-(AMINOMETHYLIDENE)-3-OXOBUTYRIC ACID ESTERS

(75) Inventors: Thomas Zierke, Böhl-Iggelheim (DE); Volker Maywald, Ludwigshafen (DE); Michael Rack, Eppelheim (DE); Sebastian Peer Smidt, Oftersheim (DE); Michael Keil, Freinsheim (DE); Bernd Wolf, Fußgönheim (DE); Christopher Koradin, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 288 days.

This patent is subject to a terminal disclaimer.

(21) Appl. No.: 12/990,364

(22) PCT Filed: Apr. 30, 2009

(86) PCT No.: PCT/EP2009/055285
§ 371 (c)(1),
(2), (4) Date: Oct. 29, 2010

(87) PCT Pub. No.: WO2009/133179
PCT Pub. Date: Nov. 5, 2009

(65) Prior Publication Data
US 2011/0040096 A1    Feb. 17, 2011

(30) Foreign Application Priority Data
May 2, 2008    (EP) .................................. 08155611

(51) Int. Cl.
*C07D 295/145*    (2006.01)
*C07D 211/34*    (2006.01)
*C07D 265/30*    (2006.01)

(52) U.S. Cl.
USPC ............................ 546/248; 544/171; 564/468

(58) Field of Classification Search
USPC ............................ 546/248; 564/468; 544/171
See application file for complete search history.

(56) References Cited

U.S. PATENT DOCUMENTS

| | | | |
|---|---|---|---|
| 5,093,347 A | 3/1992 | Graneto et al. | |
| 5,330,995 A | 7/1994 | Eicken et al. | |
| 5,340,837 A | 8/1994 | Hall et al. | |
| 5,438,070 A | 8/1995 | Eicken et al. | |
| 5,498,624 A | 3/1996 | McLoughlin et al. | |
| 5,618,951 A | 4/1997 | Britton | |
| 6,706,911 B1 * | 3/2004 | Lui et al. ................. | 560/219 |
| 7,358,387 B2 | 4/2008 | Lantzsch et al. | |
| 7,388,097 B2 | 6/2008 | Elbe et al. | |
| 7,501,527 B2 | 3/2009 | Lantzsch et al. | |
| 7,521,397 B2 | 4/2009 | Dunkel et al. | |
| 7,585,998 B2 | 9/2009 | Gallenkamp et al. | |
| 7,863,460 B2 | 1/2011 | Aihara et al. | |
| 7,939,673 B2 | 5/2011 | Pazenok et al. | |
| 7,994,207 B2 | 8/2011 | Zierke et al. | |
| 8,115,012 B2 | 2/2012 | Sukopp et al. | |
| 2005/0033095 A1* | 2/2005 | Nappa et al. ................. | 568/674 |
| 2005/0234244 A1* | 10/2005 | Bartolini et al. ............ | 548/465 |
| 2006/0252944 A1 | 11/2006 | Lantzsch et al. | |
| 2006/0276656 A1 | 12/2006 | Lantzsch et al. | |
| 2008/0108686 A1 | 5/2008 | Gewehr et al. | |
| 2009/0105316 A1 | 4/2009 | Dunkel et al. | |
| 2010/0022782 A1 | 1/2010 | Zierke et al. | |
| 2010/0069646 A1 | 3/2010 | Sukopp et al. | |
| 2010/0174094 A1 | 7/2010 | Zierke et al. | |

(Continued)

FOREIGN PATENT DOCUMENTS

| | | |
|---|---|---|
| EP | 0545099 | 6/1993 |
| EP | 0581725 | 2/1994 |

(Continued)

OTHER PUBLICATIONS

Aldabbagh, F. "Acid halides." in Comprehensive Organic Functional Group Transformations II, 2005 vol. 5, 1-17, Katritzky, Alan R.; Taylor, Richard J. K. Eds. Elsevier Ltd.: Oxford, UK.*

(Continued)

*Primary Examiner* — David K O Dell
(74) *Attorney, Agent, or Firm* — Brink Gilson & Lione

(57) ABSTRACT

The present invention relates to a process for preparing 2-(aminomethylidene)-4,4-dihalo-3-oxobutyric esters of the formula (I), (I)

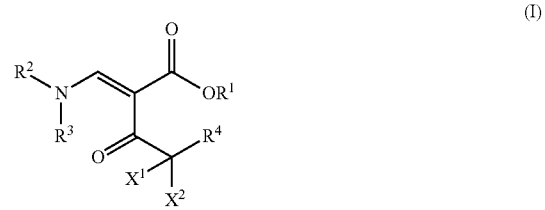

wherein $R^1$, $R^2$, $R^3$ are $C_1$-$C_6$-alkyl, $C_1$-$C_6$-haloalkyl, $C_2$-$C_6$-alkenyl, $C_3$-$C_{10}$-cycloalkyl or benzyl, and/or $R^2$ together with $R^3$ and the nitrogen atom to which the two radicals are attached are a heterocyclic radical, in which a corresponding 3-aminoacrylic ester is reacted with a halogen-substituted acetyl fluoride in the presence of at least one alkali or alkaline earth metal fluoride; and the further conversion of halogen-substituted 2-(aminomethylidene)-3-oxobutyric esters of the formula (I) to halomethyl-substituted pyrazol-4-ylcarboxylic acids and their esters.

16 Claims, No Drawings

(56) References Cited

U.S. PATENT DOCUMENTS

| | | |
|---|---|---|
| 2010/0184994 A1 | 7/2010 | Nett et al. |
| 2010/0204483 A1 | 8/2010 | Pazenok et al. |
| 2010/0215777 A1 | 8/2010 | Pohlman et al. |
| 2010/0274049 A1 | 10/2010 | Lui et al. |
| 2011/0040096 A1 | 2/2011 | Zierke et al. |
| 2011/0046371 A1 | 2/2011 | Zierke et al. |
| 2011/0172436 A1 | 7/2011 | Wolf et al. |

FOREIGN PATENT DOCUMENTS

| | | |
|---|---|---|
| EP | 0589301 | 3/1994 |
| EP | 1854788 | 11/2007 |
| EP | 2042482 | 4/2009 |
| EP | 2072497 | 6/2009 |
| JP | 266612 | 2/1989 |
| JP | 2000/212166 | 8/2000 |
| JP | 01113371 | 4/2001 |
| WO | WO 92/12970 | 8/1992 |
| WO | WO 93/11117 | 6/1993 |
| WO | WO 03/061820 | 6/2003 |
| WO | WO 03/066610 | 8/2003 |
| WO | WO 03/070705 | 8/2003 |
| WO | WO 2005/003077 | 1/2005 |
| WO | WO 2005/044804 | 5/2005 |
| WO | WO 2005/123690 | 12/2005 |
| WO | WO 2006/024389 | 3/2006 |
| WO | WO 2005/042468 | 6/2006 |
| WO | WO 2006/090778 | 8/2006 |
| WO | WO 2007/003603 | 1/2007 |
| WO | WO 2007/006806 | 1/2007 |
| WO | WO 2007/031323 | 3/2007 |
| WO | WO 2007/147888 | 12/2007 |
| WO | WO 2008/022777 | 2/2008 |
| WO | WO 2008/053043 | 5/2008 |
| WO | WO 2008/077907 | 7/2008 |
| WO | WO 2008/113660 | 9/2008 |
| WO | WO 2008/145740 | 12/2008 |
| WO | WO 2008/152138 | 12/2008 |
| WO | WO 2009/133178 | 11/2009 |
| WO | WO 2009/135808 | 11/2009 |
| WO | WO 2010/009990 | 1/2010 |

OTHER PUBLICATIONS

Altenbach, Robert J. et al., "Synthesis, Potency, and In Vivo Profiles of Quinoline Containing Histamine $H_3$ Receptor Inverse Agonists", J. Med. Chem., vol. 50, 2007, pp. 5439-5448.

Etsuji, Okada, et al., "Facile synthetic methods for 3- and 5-trifluoromethyl-4-trifluoroacetyl-pyrazoles and their conversion into pyrazole-4-carobxylic acids", Heterocycles, vol. 34, No. 4, 1992, pp. 791-798.

Nagarajan, K., et al., "Synthesis abd Structures of Pyrazoles from Ethoxymethylene Derivatives of 1,3-dicarbonyl Compounds and Hydrazines", J. Chem. Research, 1986, p. 166-167, vol. 5.

Vinogradova, N.B., et al., "Synthesis and Mechanism of the Formation of Bis(Methylamides) of Pyrazoledicarboxylic Acids, Chemistry of Heterocyclic Compounds", Jan. 1, 1968, vol. 4, pp. 502-507.

International Preliminary Report on Patentability, issued in PCT/EP2009/055285, dated Nov. 17, 2010.

International Search Report, Issued in PCT/EP2009/055285, dated Dec. 23, 2009.

Pryadeina et al., "Synthesis and Structure of 2-ethoxy- and 2-aminomethylidene 3-fluoroalkyl-3-oxopropionates," Russian Journal of Organic Chemistry, vol. 43, No. 7, (2007), pp. 945-955 (XP002557997).

\* cited by examiner

METHOD FOR THE PRODUCTION OF HALOGEN-SUBSTITUTED 2-(AMINOMETHYLIDENE)-3-OXOBUTYRIC ACID ESTERS

This application is a National Stage application of International Application No. PCT/EP2009/055285, filed Apr. 30, 2009, the entire contents of which is hereby incorporated herein by reference. This application also claims priority under 35 U.S.C. §119 to European Patent Application No. 08155611.0, filed May 2, 2008, the entire contents of which is hereby incorporated herein by reference.

The present invention relates to a process for preparing halogen-substituted 2-(aminomethylidene)-3-oxobutyric ester and its conversion to 3-halomethylpyrazol-4-ylcarboxylic acids and esters thereof. The present invention also relates to halogen-substituted 2-(aminomethylidene)-3-oxobutyric esters.

WO 92/12970 describes (3-difluoromethyl-1-methylpyrazol-4-yl)carboxamides and their use as fungicides. The preparation starts with a 4,4-difluoro-3-oxobutyric ester which is reacted successively with triethyl orthoformiate and with methylhydrazine, which gives a 3-difluoromethyl-1-methylpyrazol-4-carboxylic ester. This is then hydrolyzed to give the corresponding carboxylic acid. This is converted into the corresponding acid chloride and then, using a suitable amine, into the corresponding amide. However, providing the 4,4-difluoro-3-oxobutyric ester required as starting material is relatively expensive and difficult.

WO 2005/044804 describes alkyl esters of fluoromethyl-substituted heterocyclic carboxylic acids and their preparation by halogen exchange on corresponding chloromethyl-substituted heterocyclic carboxylic esters using fluorinating agents. However, the use of fluorinating agents is expensive, and special demands with regard to safety measures which have to be taken and to the apparatus used have to be met.

WO 2005/042468 describes the preparation of 2-(dialkylaminomethylidene)-4,4-dihalo-3-oxobutyric esters by reacting dialkylaminoacrylic esters with dihaloacetyl halides in the presence of a base. Here, in order to prevent the formation of dihaloketenes, the bases used are in particular aqueous solutions of alkali metal and alkaline earth metal hydroxides. However, this reaction does not give satisfactory yields. The 2-(dialkyl-aminomethylidene)-4,4-dihalo-3-oxobutyric esters obtained are converted with $C_1$-$C_4$-alkylhydrazines into the corresponding N-alkylated dihalomethyl-substituted pyrazol-4-ylcarboxylic esters. However, this reaction provides no satisfactory selectivity for the 3-dihalomethyl compound over the corresponding 5-dihalomethyl compound. The subsequent separation of the two isomers formed is relatively complicated.

Accordingly, it is an object of the present invention to provide a process for providing starting materials for preparing 3-halomethylpyrazol-4-ylcarboxylic esters and their derivatives, resulting in the starting materials being obtained at low expense and in high yields. Furthermore, from the starting materials, it should be possible to prepare the 3-halomethylpyrazol-4-ylcarboxylic esters in high yield, with a selectivity which is as high as possible, over the reaction to the 5-halomethylpyrazol-4-ylcarboxylic ester, which usually takes place as a side reaction.

Surprisingly, it has been found that this object is achieved by a process for preparing compounds of the formula (I)

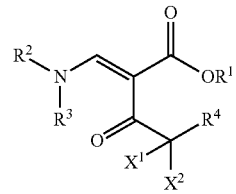

in which
$R^1$ is $C_1$-$C_6$-alkyl, $C_1$-$C_6$-haloalkyl, $C_2$-$C_6$-alkenyl, $C_3$-$C_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
$R^2$ and $R^3$ independently of one another are $C_1$-$C_6$-alkyl, $C_1$-$C_6$-haloalkyl, $C_2$-$C_6$-alkenyl, $C_3$-$C_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; or
$R^2$ together with $R^3$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members;
$R^4$ is hydrogen, fluorine or chlorine; and
$X^1$ and $X^2$ independently of one another are fluorine or chlorine;
wherein a compound of the formula (II)

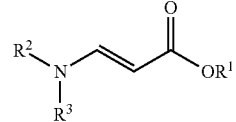

in which $R^1$, $R^2$ and $R^3$ have one of the meanings given above; is reacted with a compound of the formula $X^1X^2R^4C$—C(=O)—F in the presence of at least one alkali or alkaline earth metal fluoride.

By this process according to the invention, it is possible to provide particularly suitable starting materials for a process for preparing 3-halomethylpyrazol-4-yl)carboxylic esters with low expenses and in high yields.

The E configuration shown here and in the formulae of the compounds I and II below of the C═C double bond is only one possible embodiment of the compounds I and II. The invention relates both to the E isomer shown and to the Z isomer and in particular to mixtures of the isomers.

The terms for organic groups used in the definition of the variables, such as, for example, the term "halogen", are collective terms which represent the individual members of these groups of organic moieties.

In each case, the prefix $C_x$-$C_y$ denotes the number of possible carbon atoms.

In each case, the term "halogen" denotes fluorine, bromine, chlorine or iodine, especially fluorine, chlorine or bromine.

The term "$C_1$-$C_6$-alkyl", as used herein and in the alkyl moieties of $C_1$-$C_6$-alkoxy, denotes a saturated straight-chain or branched hydrocarbon group comprising 1 to 6 carbon atoms, especially 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and isomers thereof. $C_1$-$C_4$-alkyl comprises, for example, methyl, ethyl, propyl, 1-methylethyl, butyl, 1-methylpropyl, 2-methylpropyl and 1,1-dimethylethyl.

The term "$C_1$-$C_6$-alkoxy" describes straight-chain or branched saturated alkyl groups comprising 1 to 6 carbon atoms, which groups are attached via an oxygen atom. Examples of $C_1$-$C_6$-alkoxy include methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Examples of $C_1$-$C_4$-alkoxy include methoxy, ethoxy, n-propoxy, 1-methylethoxy, n-butoxy, 1-methylpropoxy, 2-methylpropoxy and 1,1-dimethylethoxy.

The term "$C_1$-$C_6$-haloalkyl", as used herein and in the haloalkyl moieties of $C_1$-$C_6$-haloalkoxy, describes straight-chain or branched alkyl groups having 1 to 6 carbon atoms, where some or all of the hydrogen atoms of these groups are replaced by halogen atoms. Examples of these are $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

The term "$C_1$-$C_6$-haloalkoxy" describes straight-chain or branched saturated haloalkyl groups comprising 1 to 6 carbon atoms, which groups are attached via an oxygen atom. Examples of these are $C_1$-$C_4$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy.

The term "$C_2$-$C_6$-alkenyl" describes straight-chain and branched unsaturated hydrocarbon groups comprising 2 to 6 carbon atoms and at least one carbon-carbon double bond, such as, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_3$-$C_{10}$-cycloalkyl", as used herein, describes mono-, bi- or tricyclic hydrocarbon groups comprising 3 to 10 carbon atoms, especially 3 to 6 carbon atoms. Examples of monocyclic groups include cyclopropyl, cyclobutyl, cyclopentyl, cyclohexyl, cycloheptyl or cyclooctyl. Examples of bicyclic groups include bicyclo[2.2.1]heptyl, bicyclo[3.1.1]heptyl, bicyclo[2.2.2]octyl and bicyclo[3.2.1]octyl. Examples of tricyclic groups are adamantyl and homoadamantyl.

In connection with the definition of the group —$NR^2R^3$, the term "5- to 10-membered heterocyclic radical" denotes a nitrogenous mono- or bicyclic group having 5, 6, 7, 8, 9 or 10 ring members, which is attached via the nitrogen atom to the remainder of the compound of the formula (I) or (II), which, in addition to the nitrogen atom, may have a further 1, 2 or 3 heteroatoms selected from the group consisting of O, N and S as ring members and which is unsubstituted or may have 1, 2 or 3 substituents. The substituents, provided they are attached to a carbon atom of the heterocyclic radical, are preferably selected from the group consisting of halogen, CN, $C_1$-$C_4$-haloalkyl, $C_1$-$C_4$-alkoxy and $C_1$-$C_4$-haloalkoxy and, provided they are attached to a further nitrogen atom of the heterocyclic radical, are preferably selected from the group consisting of $C_1$-$C_4$-alkyl and $C_1$-$C_4$-haloalkyl. Examples of 5- to 10-membered heterocyclic radicals are pyrrol-1-yl, pyrrolidin-1-yl, oxazolidin-3-yl, thiazolidin-3-yl, imidazol-1-yl, imidazolin-1-yl, 3-methylimidazolin-1-yl, 3-ethylimidazolin-1-yl, 3-propylimidazolin-1-yl, 3-(1-methylethyl)imidazolin-1-yl, 3-butylimidazolin-1-yl, 3-(1,1-dimethylethyl)imidazolin-1-yl, pyrazol-1-yl, pyrazolidin-1-yl, 2-methylpyrazolidin-1-yl, 2-ethylpyrazolidin-1-yl, 2-propylpyrazolidin-1-yl, 2-(1-methylethyl)pyrazolidin-1-yl, 2-butylpyrazolidin-1-yl, 2-(1,1-dimethylethyl)pyrazolidin-1-yl, piperidin-1-yl, morpholin-4-yl, thiamorpholin-4-yl, piperazin-1-yl, 4-methylpiperazin-1-yl, 4-ethylpiperazin-1-yl, 4-propylpiperazin-1-yl, 4-(1-methylethyl)piperazin-1-yl, 4-butylpiperazin-1-yl, 4-(1,1-dimethylethyl)piperazin-1-yl, indol-1-yl, indolin-1-yl, isoindol-1-yl, isoindolin-1-yl, indazol-1-yl, indazolin-1-yl, 2-methylindazolin-1-yl, indazolin-2-yl and 1-methylindazolin-1-yl, where the heterocyclic groups mentioned above are unsubstituted, or 1, 2 or 3 of the ring carbon atoms carry a substituent selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy.

The carbon-carbon double bond in the compounds of the formulae (I) and (II) can have the E or the Z configuration (or the cis or trans configuration, based on the relative arrangement of the group $NR^2R^3$ and the group —$C(O)OR^1$).

The reactions described herein are carried out in reaction vessels customary for such reactions, where the reaction may be carried out either continuously or batchwise. In general, the reactions in question will be carried out at atmospheric pressure. However, the reactions can also be carried out under superatmospheric pressure.

In the compounds of the formulae (I) and (II), $R^1$ is preferably $C_1$-$C_6$-alkyl, $C_3$-$C_{10}$-cycloalkyl or benzyl, where the two last mentioned radicals are unsubstituted or have 1, 2 or 3 substituents. Preferably, $R^1$ in the compounds of the formulae (I) and (II) is $C_1$-$C_4$-alkyl, $C_3$-$C_6$-cycloalkyl or benzyl. Very particularly preferably, $R^1$ in the compounds of the formulae (I) and (II) is $C_1$-$C_4$-alkyl.

In the compounds of the formulae (I) and (II), $R^2$ and $R^3$ independently of one another are preferably $C_1$-$C_4$-alkyl, or $R^2$ together with $R^3$ and the nitrogen atom to which the two radicals are attached are an optionally substituted 5- to 10-membered heterocyclic radical which, in addition to the nitrogen atom, may comprise a further 1, 2 or 3 heteroatoms selected from the group consisting of O, N and S as ring members.

Particularly preferably, $R^2$ and $R^3$ together with the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members, i.e. the group $NR^2R^3$ is a 5- to 10-membered heterocyclic radical which is attached via nitrogen. These preferences apply both to the compounds of the formulae (I) and (II) per se and to their use in the process according to the invention for preparing 3-halomethylpyrazol-4-ylcarboxylic esters.

In the compounds of the formulae (I) and (II), the group $NR^2R^3$ very particularly preferably is a saturated, optionally substituted 5- or 6-membered heterocyclic radical which, in addition to the nitrogen atom, may contain a further heteroatom selected from the group consisting of O, N and S as ring member. In particular, the group $NR^2R^3$ is pyrrolidin-1-yl, oxazolidin-3-yl, 3-methylimidazolin-1-yl, piperidin-1-yl, morpholin-4-yl or 4-methylpiperazin-1-yl. Specifically, the group $NR^2R^3$ in the compounds of the formulae (I) and (II) is piperidin-1-yl, morpholin-4-yl or 4-methylpiperazin-1-yl.

In the compounds of the formulae (I) and (II) and, as a consequence, also in the compounds of the formula $X^1X^2R^4C$—$C(=O)$—F, $R^4$ is preferably hydrogen or fluorine. Particularly preferably, $R^4$ is hydrogen.

In the compounds of the formulae (I) and (II) and, as a consequence, also in the compounds of the formula $X^1X^2R^4C$—$C(=O)$—F, $X^1$ and $X^2$ are preferably fluorine.

Suitable compounds of the formula $X^1X^2R^4C$—$C(=O)$—F are, for example, difluoroacetyl fluoride, dichloroacetyl fluoride, trifluoroacetyl fluoride, difluorochloroacetyl fluoride, dichlorofluoroacetyl fluoride and trichloroacetyl fluoride. Preferred compounds of the formula $X^1X^2R^4C$—$C(=O)$—F are difluoroacetyl fluoride, dichloroacetyl fluoride, trifluoroacetyl fluoride and difluorochloroacetyl fluoride. Particularly preferred compounds of the formula $X^1X^2R^4C$—$C(=O)$—F are difluoroacetyl fluoride, difluorochloroacetyl fluoride and trifluoroacetyl fluoride. Very particularly preferably, difluoroacetyl fluoride is used in the process according to the invention.

In the process according to the invention for preparing compounds of the formula (I), the compound of the formula (II) is usually employed in an amount of from 0.2 to 3 mol, preferably from 0.3 to 1.5 mol, particularly preferably from 0.5 to 1.0 mol, especially from 0.9 to 1.0 mol, in each case based on 1 mol of the compound of the formula $X^1X^2R^4C$—$C(=O)$—F.

The reaction is carried out by bringing the starting materials, i.e. the compound of the formula (II) and the compound of the formula $X^1X^2R^4C$—$C(=O)$—F, into contact with one another, preferably in a suitable solvent in a reaction vessel, where the compound of the formula (II) and, if appropriate, the solvent are generally initially charged in the reaction vessel.

The reaction of the compound of the formula (II) with the compound of the formula $X^1X^2R^4C$—$C(=O)$—F is usually carried out at a temperature in the range of from −70 to +50° C., preferably at from −30 to +20° C. and particularly preferably from −10 to 0° C. In a specific embodiment, the temperature is initially adjusted to from −50 to −10° C. and, during the course of the reaction, increased to from +10 to +40° C., in particular room temperature.

The reaction of the compound of the formula (II) with the compound of the formula $X^1X^2R^4C$—$C(=O)$—F is usually carried out at atmospheric pressure. However, owing to the low boiling point of the compound of the formula $X^1X^2R^4C$—$C(=O)$—F, it may, depending on the chosen reaction temperature, be advantageous to carry out the reaction under elevated pressure. Suitable reaction pressures are, for example, in a range of from 0.5 to 10 bar. Suitable pressure-resistant reactors are also known to the person skilled in the art and are described, for example, in Ullmanns Enzyklopädie der technischen Chemie [Ullmanns Encyclopedia of Industrial Chemistry], vol. 1, 3rd edition, 1951, p. 769 ff.

In the process according to the invention for preparing compounds of the formula (I), the reaction of the compound of the formula (II) with the compound of the formula $X^1X^2R^4C$—$C(=O)$—F is preferably carried out essentially anhydrously, i.e. in a dry organic solvent.

Here and below, dry solvent means that the solvent has a water content of less than 500 ppm and in particular of less than 100 ppm.

Examples of suitable organic solvents are nonpolar, aprotic solvents, for example aromatic hydrocarbons, such as benzene, toluene, xylenes, or (cyclo)aliphatic hydrocarbons, such as hexane, cyclohexane and the like, and also mixtures of the solvents mentioned above.

Examples of suitable organic solvents are likewise aprotic polar solvents, for example cyclic and acyclic ethers, such as diethyl ether, tert-butyl methyl ether (MTBE), diisopropyl ether, cyclopentyl methyl ether, tetrahydrofuran (THF) or dioxane, cyclic or acyclic amides, such as dimethyl formamide, dimethyl acetamide, N-methylpyrrolidone, ureas, such as N,N'-dimethyl-N,N'-ethyleneurea (DMEU), N,N'-dimethyl-N,N'-propyleneurea (DMPU) or tetramethylurea, or aliphatic nitriles, such as acetonitrile or propionitrile, and also mixtures of the solvents mentioned above.

Also suitable are mixtures of the nonpolar aprotic organic solvents mentioned above with polar aprotic solvents.

According to the invention, the compound of the formula (II) is reacted in the presence of at least one alkali metal or alkaline earth metal fluoride. In general, the compound of the formula (II) is reacted in the presence of at least equimolar amounts of at least one alkali metal or alkaline earth metal fluoride, based on the compound of the formula (II), i.e. in an amount of at least one mole, based on one mole of the compound (II). Preferably, the compound of the formula (II) is reacted in the presence of from 1.1 to 5 mol, particularly preferably from 1.2 to 2 mol, of at least one alkali metal or alkaline earth metal fluoride, in each case based on 1 mol of the compound of the formula (II).

Suitable alkali metal or alkaline earth metal fluorides are, for example, lithium chloride (LiF), sodium fluoride (NaF), potassium fluoride (KF), magnesium fluoride ($MgF_2$) or calcium fluoride ($CaF_2$, fluor-spar) or mixtures thereof. These can likewise be used in crystalline form, and also in amorphous form or else in an industrially prepared form, such as, for example, in spray-dried form. In the process according to the invention, preference is given to using NaF, KF or $MgF_2$ or mixtures thereof. Particularly preferably, KF is used in the process according to the invention.

The compound of the formula (II) is usually reacted with the compound of the formula $X^1X^2R^4C-C(=O)-F$ without addition of a further base different from the alkali metal or alkaline earth metal fluoride and the compound of the formula (II).

However, it is also possible to react the compound of the formula (II) with the compound of the formula $X^1X^2R^4C-C(=O)-F$ in the presence of an additional base.

Suitable additional bases are organic bases, for example acyclic tertiary amines, e.g. tri-$C_1$-$C_6$-alkylamines such as trimethylamine, triethylamine, diisopropylethylamine, tert-butyldimethylamine, N—$C_3$-$C_6$-cycloalkyl-N,N-di-$C_1$-$C_6$-alkylamines or N,N-bis-$C_3$-$C_6$-cycloalkyl-N—$C_1$-$C_6$-alkylamines such as ethyldicyclohexylamine, cyclic tertiary amines, e.g. N—$C_1$-$C_6$-alkyl-nitrogen heterocycles such as N-methylpyrrolidine, N-methylpiperidine, N-methylmorpholine, N,N'-dimethylpiperazine, pyridine compounds such as pyridine, collidine, lutidine or 4-dimethylaminopyridine, and bicyclic amines, such as diazabicycloundecene (DBU) or diazabicyclononene (DBN).

Suitable additional bases are likewise inorganic compounds, for example alkali metal and alkaline earth metal carbonates, such as lithium carbonate or calcium carbonate, alkali metal bicarbonates, such as sodium bicarbonate, alkali metal and alkaline earth metal oxides, such as lithium oxide, sodium oxide, calcium oxide or magnesium oxide, alkali metal and alkaline earth metal hydrides, such as lithium hydride, sodium hydride, potassium hydride or calcium hydride, or alkali metal amides, such as lithium amide, sodium amide or potassium amide.

If in the process according to the invention, a further base (auxiliary base) different from alkali or alkaline earth metal fluoride and from the compound of the formula (II) is added, this can be employed either in approximately equimolar amounts, based on the compound (II), for example in an amount of from about 0.8 to 1.2 mol per mole of the compound (II), or in catalytic amounts, based on the compound (II), for example in an amount of from about 0.001 to 0.2 mol per mole of the compound (II). However, the additional base can also be employed in a large excess based on the compound of the formula (II), for example as solvent. In a preferred embodiment, the auxiliary base is, if at all, employed in an amount of not more than 0.2 mol, in particular not more than 0.1 mol and especially not more than 0.05 mol, per mole of the compound (II).

Usually, the compound of the formula (I) is isolated under approximately pH-neutral conditions, i.e. at a pH in the range of from 4 to 10, or under non-aqueous conditions, in order to prevent excess hydrolysis of the group $-C(O)OR^1$.

However, for the conversion described below into the corresponding pyrazol-4-ylcarboxylic ester, it is not necessary to isolate the compounds of the formula (I). On the contrary, it has been found to be advantageous not to isolate the compound of formula (I) and to convert it as a crude product or in the form of the reaction mixture obtained in the process according to the invention into the corresponding pyrazol-4-ylcarboxylic esters.

The process according to the invention yields the compounds of the formula (I) from the compounds of the formula (II) in good to very good yields, i.e. generally in yields of at least 70% and frequently of at least 80%.

The compounds of the general formula (II) are commercially available or can be prepared analogously to known compounds, as illustrated, for example, in scheme 1 or 2.

Scheme 1

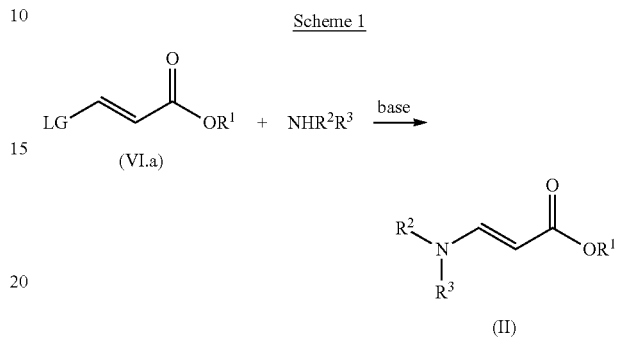

Scheme 1 shows the preparation of compounds of the formula (II) by reacting an α,β-unsaturated ester of the formula (VI.a) in which $R^1$ has one of the meanings given above and LG is a leaving group, such as, for example, an alkoxy group, e.g. $C_1$-$C_6$-alkoxy, with an amine of the formula $NHR^2R^3$ in which $R^2$ and $R^3$ have one of the meanings given above, in the presence of a base such as, for example, $K_2CO_3$. Suitable methods for carrying out this reaction are known to the person skilled in the art.

Scheme 2

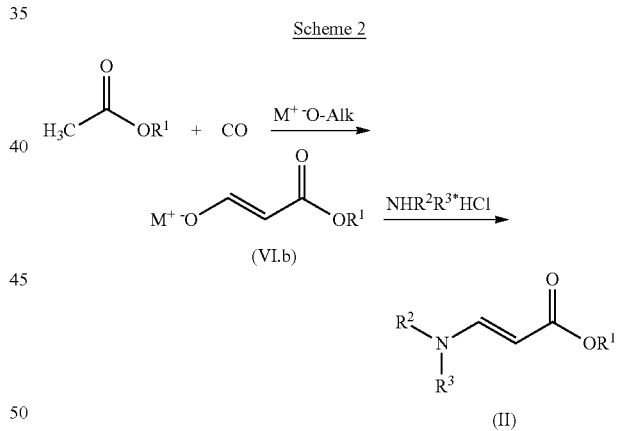

Alternatively, compounds of the formula (II) can be provided analogously to EP 0 388 744 by reacting a β-hydroxyacrylic ester salt of the formula (VI.b) in which $R^1$ has one of the meanings mentioned above and $M^+$ is, for example, an alkali metal cation, such as $Na^+$ or $K^+$, with an ammonium chloride of the formula $NHR^2R^3*HCl$.

Compounds of the formula (VI.b) can be provided, for example, by reacting the corresponding acetic ester with CO and an alkoxide of the formula $M^+$-O-Alk, in which Alk is, for example, $C_1$-$C_4$-alkyl.

When converting the compounds of the formula (I) into halomethyl-substituted pyrazolylcarboxylic esters, the amines of the formula $NHR^2R^3$ are obtained as a byproduct, and after the reaction has been carried out, they can advantageously be recovered and, if appropriate, converted into their hydrochlorides NHR²R³*HCl, to be used again for providing compounds of the formula (II) according to scheme 1 or 2.

The compounds of the formula (I), prepared by the process according to the invention, in which R² together with R³ and the nitrogen atom to which the two radicals are attached are a heterocyclic radical are likewise novel. These novel compounds of the formula (I) can be provided in particularly good yields and are particularly suitable for reaction with N-substituted hydrazine compounds to give 3-halomethylpyrazol-4-ylcarboxylic esters, especially with a view to the yield and the selectivity of the desired isomer over the 5-halomethylpyrazol-4-ylcarboxylic ester formed as byproduct.

Accordingly, another subject matter of the invention relates to the compounds of the formula (I)

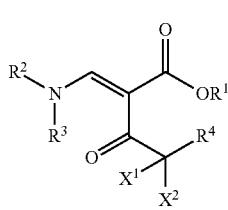

(I)

in which $R^1$, $R^4$, $X^1$ and $X^2$ have one of the meanings given above and $R^2$ together with $R^3$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members. With regard to preferred meanings of the radicals $R^1$, $R^4$, $X^1$ and $X^2$, what was said above in the context of the processes according to the invention is fully incorporated herein.

The compounds of the formula (I) are suitable in a particularly advantageous manner for preparing halomethyl-substituted pyrazol-4-ylcarboxylic esters.

Accordingly, a further subject matter of the invention relates to a process for preparing halomethyl-substituted pyrazol-4-ylcarboxylic esters of the formula (III)

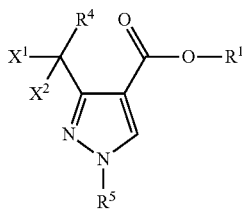

(III)

in which
$R^1$ is $C_1$-$C_6$-alkyl, $C_1$-$C_6$-haloalkyl, $C_2$-$C_6$-alkenyl, $C_3$-$C_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
$R^4$ is hydrogen, fluorine or chlorine;
$R^5$ is hydrogen, $C_1$-$C_6$-alkyl, $C_1$-$C_6$-haloalkyl, $C_3$-$C_{10}$-cycloalkyl, phenyl or benzyl where the three last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; and
$X^1$ and $X^2$ are independently of one another fluorine or chlorine;
comprising
a) the provision of a compound of the formula (I) by means of the above described inventive process, and
b) the reaction of the compound of the formula (I) provided with a hydrazine compound of the formula (IV)

$$R^5HN\text{—}NH_2 \qquad (IV)$$

in which $R^5$ has one of the meanings given above.

The process according to the invention for preparing compounds of the formula (III) is associated with a number of advantages. In particular if $R^2$ and $R^3$ together with the nitrogen atom to which the two radicals are attached are a heterocyclic radical. The process according to the invention affords the compounds of the formula (III) in a high yield. Moreover, if $R^5$ has a meaning different from H, the compound of the formula (III) is prepared with high selectivity over the 5-halomethylpyrazol-4-yl)carboxylic ester formed as a byproduct. Thus, a complicated separation of the isomer mixtures may be dispensed with or at least limited. Moreover, the process according to the invention can be carried out both anhydrously and in the presence of water, simultaneously achieving satisfactory yields and excesses of the compound of the formula (III).

Preferably, the group $R^1$ in the compounds of the formula (III) has one of the meanings mentioned above as preferred meanings of the groups $R^1$ in the compounds of the formulae (I) and (II).

In a specific embodiment of the process according to the invention, the group $R^5$ in the compounds of the formulae (III) and (IV) has a meaning different from hydrogen. By the process according to the invention, the compounds of the formula (III) in which $R^5$ has a meaning different from hydrogen can be prepared with particularly high selectivity over the corresponding 5-halomethylpyrazol-4-ylcarboxylic esters.

Preferably, the group $R^5$ in the compounds of the formulae (III) and (IV) is $C_1$-$C_4$-alkyl, $C_3$-$C_6$-cycloalkyl, phenyl or benzyl, where the three last mentioned radicals are unsubstituted or have 1, 2 or 3 substituents independently of one another selected from the group consisting of halogen, $C_1$-$C_4$-alkyl and $C_1$-$C_4$-alkoxy. With particular preference, $R^5$ in the compounds of the formulae (III) and (IV) is $C_1$-$C_6$-alkyl, in particular $C_1$-$C_4$-alkyl and especially methyl.

In a specific embodiment of the process according to the invention for preparing compounds of the formula (III), the compound of formula (I) is provided in the form of a reaction mixture which is prepared by the inventive process described above without thereby isolating the compound of the formula (I), i.e. the preparation of the compounds of formula (III) and their reaction with the hydrazine compound of the formula (IV) takes place in a concentrated manner in a so-called one pot process.

Step b)

Preferably, the hydrazine compound of the formula (IV) is employed in equimolar amounts or in excess, based on the component of the formula (I), a relatively large excess of the compound (IV), for example of more than 20 mol %, generally not being required. Preferably, from 1.0 to 1.2 mol, in particular from about 1.01 to 1.15 mol, of the hydrazine compound (IV) are employed per mole of the compound (I).

The hydrazine compound of the formula (IV) is preferably a $C_1$-$C_6$-alkylhydrazine and in particular a $C_1$-$C_4$-alkylhydrazine; specifically, the compound of the general formula (IV) is methylhydrazine.

If $R^5$ in the compounds of the formula (III) is hydrogen, the compound of the formula (IV) used is preferably hydrazine hydrate.

The reaction of the compound of the formula (I) with the hydrazine compound (IV) is usually carried out such that the hydrazine compound of the formula (IV) is initially charged in a suitable solvent, the desired reaction temperature is set and the compound of the formula (I), if appropriate in the form of a solution and/or a reaction mixture obtained during the provision, is then added.

Preferably, the hydrazine compound of the formula (IV) is initially charged as a solution in an organic solvent or a solvent/water mixture. Alternatively, it may also be possible to add the hydrazine compound of the formula (IV), preferably as solution in an organic solvent or in a solvent/water mixture, to the compound of the formula (I), if appropriate in the form of a solution in an organic solvent or in a solvent/water mixture.

Organic solvents suitable for reacting the compound of the formula (I) with the hydrazine compound (IV) are, for example, protic polar solvents, such as aliphatic alcohols having preferably 1 to 4 carbon atoms, especially methanol, ethanol, n-propanol, isopropanol, n-butanol, isobutanol or tert-butanol, nonpolar aprotic solvents, e.g. aromatic hydrocarbons, such as benzene, toluene, xylenes, mesitylene, cumene, chlorobenzene, nitrobenzene or tert-butylbenzene, aprotic polar solvents, such as cyclic or acyclic ethers, especially diethyl ether, tert-butyl methyl ether (MTBE), cyclopentyl methyl ether, tetrahydrofuran (THF) or dioxane, cyclic or acyclic amides, especially dimethylformamide, dimethylacetamide, N-methylpyrrolidone, ureas, such as N,N'-dimethyl-N,N'-ethyleneurea (DMEU), N,N'-dimethyl-N,N'-propyleneurea (DMPU) or tetramethylurea, or aliphatic nitriles, especially acetonitrile or propionitrile, or mixtures of the solvents mentioned above.

The reaction of the compound of the formula (I) with the hydrazine compound (IV) can, if appropriate, be carried out in the presence of a base.

Bases suitable for this purpose are organic bases, for example the abovementioned acyclic tertiary amines, such as trimethylamine, triethylamine, diisopropylethylamine, tert-butyldimethylamine or ethyldicyclohexylamine, the abovementioned cyclic tertiary amines, such as N-methylpyrrolidine, N-methylpiperidine, N-methylmorpholine, N,N'-dimethylpiperazine, pyridine, collidine, lutidine or 4-dimethylaminopyridine, or bicyclic amines, such as diazabicycloundecene (DBU) or diazabicyclononene (DBN).

Also suitable as bases are inorganic compounds, for example alkali metal and alkaline earth metal hydroxides, such as sodium hydroxide, potassium hydroxide or calcium hydroxide, alkali metal and alkaline earth metal oxides, such as lithium oxide, sodium oxide, calcium oxide or magnesium oxide, alkali metal and alkaline earth metal carbonates, such as lithium carbonate or calcium carbonate, alkali metal bicarbonates, such as sodium bicarbonate, alkali metal and alkaline earth metal hydrides, such as lithium hydride, sodium hydride, potassium hydride or calcium hydride, or alkali metal amides, such as lithium amide, sodium amide or potassium amide.

The base can be employed either in approximately equimolar amounts, based on the compound (I), for example in an amount of from about 0.8 to 1.2 mol per mole of the compound (I), or in catalytic amounts, based on the compound (I), for example in an amount of from about 0.001 to 0.2 mol per mole of the compound (I). However, the base may also be employed in a large excess based on the compound of the formula (II), for example as solvent.

By adding a base, it may, if appropriate, be possible to achieve a relatively large excess of the 3-halomethylpyrazol-4-ylcarboxylic esters of the formula (III), based on the 5-halomethylpyrazol-4-ylcarboxylic ester formed as byproduct.

In a specific embodiment of the process according to the invention for preparing compounds of the formula (III), the reaction of the compound of the formula (I) with the hydrazine compound of the formula (IV) is carried out in the presence of water. Here, even a small amount of water in the reaction mixture of 1000 ppm is sufficient. The water released during the reaction is not taken into account when the water content is stated.

In general, the water content of the reaction mixture will not exceed 50% by volume, frequently 30% by volume, in particular 15% by volume, and it is frequently in the range of from 0.1 to 50% by volume, preferably in the range of from 0.5 to 30% by volume, in particular in the range of from 1 to 15% by volume.

The reaction of the compound of the formula (I) is usually carried out in the presence of water at temperatures of from −80 to +100° C. In a specific embodiment, at the start of the reaction, the temperature is set to from −50 to +20° C., in particular from −15 to +10° C., and during the course of the reaction it is increased to a temperature of from +10 to +40° C., in particular to room temperature.

If the reaction of the compound of the formula (I) is carried out in the presence of water and a base, the base is preferably selected from the inorganic compounds mentioned above, specifically from the alkali metal or alkaline earth metal bases mentioned above and in particular from alkali metal hydroxides or alkaline earth metal hydroxides, such as NaOH or KOH. With respect to the amounts used, what was said above applies.

The process according to the invention affords the compounds of the formula (III), when reacting a compound of the formula (I) in the presence of water, in good yields, i.e. generally in yields of at least 60% and frequently of at least 70%. Furthermore, if $R^5$ has a meaning different from H, this embodiment of the process yields the compounds of the formula (III) with high selectivity over the corresponding 5-halomethylpyrazol-4-ylcarboxylic esters, i.e. generally in a ratio of 3-halomethylpyrazol-4-ylcarboxylic ester to 5-halomethylpyrazol-4-ylcarboxylic ester of at least 2.5:1 and frequently of at least 5:1. In the presence of a suitable base, ratios of at least 10:1 or even 20:1 are frequently obtained.

In a further specific embodiment of the process according to the invention for preparing compounds of the formula (III), the reaction of the compound of the formula (I) with the hydrazine compound of the formula (IV) is carried out essentially anhydrously, i.e. the reaction mixture has a water content of less than 500 ppm and in particular of less than 100 ppm. The water released during the reaction is not taken into account in the stated water content.

Usually, the process according to the invention in which the reaction of a compound of the formula (I) is carried out essentially anhydrously is carried out at temperatures of from −80 to +100° C. In a specific embodiment, at the beginning of the reaction the temperature is set to from −80 to −10° C., in particular from −60 to −30° C., and increased during the course of the reaction to a temperature of from +10 to +40° C., in particular room temperature.

If the process according to the invention in which the reaction of a compound of the formula (I) is carried out essentially anhydrously is carried out in the presence of a base, this base is preferably selected from among alkaline earth metal and alkali metal carbonates and the organic bases mentioned above, in particular from among the organic bases and specifically from among the pyridines and acyclic tertiary amines mentioned above, such as pyridine or triethylamine. With respect to the amount employed, what was said above applies.

The process according to the invention in which the reaction of a compound of the formula (I) is carried out essentially anhydrously affords the compounds of the formula (III) in good to very good yields, i.e. generally in yields of at least 80% and frequently of at least 90%. Furthermore, if $R^5$ has a meaning different from H, this embodiment of the process yields the compounds of the formula (III) with very high selectivity over the corresponding 5-halomethylpyrazol-4-ylcarboxylic esters, i.e. generally in a ratio of 3-halomethylpyrazol-4-ylcarboxylic ester to 5-halomethylpyrazol-4-ylcarboxylic ester of at least 10:1 and frequently of at least 20:1.

Work-up of the reaction mixtures obtained and isolation of the compound of the formula (III) is carried out in a customary manner, for instance by removing the solvent, for example under reduced pressure, by aqueous extractive work-up or by a combination of these measures. Further purification may be carried out, for example, by a crystallization or by chromatography. Frequently, the product is already obtained in a purity which makes further purification steps redundant.

When converting the compounds of the formula (I) into halomethylpyrazolylcarboxylic esters, the amines of the formula $NHR^2R^3$ are obtained as a byproduct. These amines can be isolated by suitable measures known to the person skilled in the art and be used for providing compounds of the formula (II). The isolation of the amines of the formula $NHR^2R^3$ can be carried out, for example, by customary separation methods, such as precipitation by adjusting the pH, or by extraction.

The compounds of the formula (III) can be hydrolyzed to give the corresponding difluoromethyl-substituted pyrazol-4-ylcarboxylic acids.

Accordingly, a further subject matter of the invention relates to a process for preparing a pyrazol-4-carboxylic acid of the formula (V)

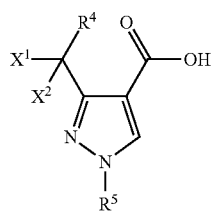

(V)

in which $R^4$, $R^5$, $X^1$ and $X^2$ have one of the meanings given above, comprising the provision of a compound of the formula (III) as defined above by a process according to the invention and hydrolysis of the ester function in the compound of the formula (III) provided, whereby the pyrazolecarboxylic acid of the formula (V) is obtained.

In a specific embodiment of the process according to the invention for preparing compounds of the formula (V), the compounds of the formula (III) are prepared in the form of a reaction mixture provided by a process according to the invention without isolating the compound of the formula (III), i.e. the preparation of the compound of the formula (III) and its reaction by means of hydrolysis to form a compound of the formula (V) take place in a concentrated manner in a so-called one pot process.

The hydrolysis of the ester function in the compound (III) can be carried out with acid catalysis or basically or in another way. The compound (III) can be employed as such, i.e. after isolation. However, it is also possible to react the reaction mixture obtained in step b), if appropriate after removal of volatile components, such as solvents, without isolation of the compound of the formula (III).

In the basic hydrolysis of the compound (III), the compound of the formula (III) is usually treated with an alkali metal hydroxide or alkaline earth metal hydroxide, such as sodium hydroxide, potassium hydroxide or lithium hydroxide, preferably with an aqueous alkali metal hydroxide solution or alkaline earth metal hydroxide solution, specifically an aqueous NaOH solution or an aqueous KOH solution, until the ester is completely hydrolyzed, preferably with heating.

In the basic hydrolysis, the molar ratio of the compound of the formula (III) to the base is usually in the range of from 0.8:1 to 1:10 and is in particular about equimolar, for example in the range of from 0.8:1 to 1.2:1; however, a relatively large excess of base, for example of up to 5 mol per mole of the compound (III), may also be advantageous.

The basic hydrolysis is usually carried out in a diluent or solvent. In addition to water, suitable diluents or solvents are also mixtures of organic solvents stable towards alkali, with water. Examples of organic solvents which are stable to alkali are in particular the $C_1$-$C_4$-alcohols mentioned above, and also the acyclic and cyclic ethers mentioned above.

Also suitable are mixtures of nonpolar solvents, for example aromatic hydrocarbons, such as benzene, toluene, xylenes, or (cyclo)aliphatic hydrocarbons, such as hexane, cyclohexane and the like, with water.

The basic hydrolysis is preferably carried out at temperatures of from 20 to 100° C. In general, the upper temperature limit is the boiling point of the solvent used, provided the reaction is carried out at atmospheric pressure. Preferably, a reaction temperature of 100° C. and in particular of 90° C. is not exceeded. Here, the reaction time depends on the reaction temperature and on the concentration and the stability of the ester compound in question. In general, the reaction conditions are chosen such that the reaction time is in the range of from 0.5 to 12 h and in particular in the range of from 1 to 6 h.

The acidic hydrolysis of the ester group of the compound (III) can be carried out analogously to known acidic ester hydrolyses, i.e. in the presence of catalytic or stoichiometric amounts of an acid and water (see, for example, J. March, Advanced Organic Chemistry, 2nd ed., 334-338, McGraw-Hill, 1977 and the literature cited therein). Frequently, the reaction is carried out in a mixture of water and an aprotic organic solvent, for example an ether, as mentioned above. Examples of suitable acids are hydrohalic acids, sulfuric acid, organic sulfonic acids, such as p-toluenesulfonic acid or methanesulfonic acid, phosphoric acid and also acidic ion exchange resins and the like.

Suitable hydrolysis catalysts are furthermore alkali metal iodides, lithium iodide, trimethyliodosilane or mixtures of trimethylchlorosilane with alkali metal iodides, such as lithium iodide, sodium iodide or potassium iodide.

The acid (V) is isolated by customary separation methods, such as, for example, by precipitation via adjusting the pH, or by extraction.

It has been found to be particularly advantageous, when using mixtures of nonpolar solvents with water as reaction medium, to separate the acid of the formula (V) under basic pH conditions as a solution in the aqueous phase, followed by precipitation as a solid from the aqueous solution by adjusting an acidic pH. If the compounds of the formula (III) are hydrolyzed in the form of a reaction mixture provided by a process according to the invention, without prior isolation of the compound of the formula (III), this procedure affords, as a byproduct of the precursor, the amine of the formula NHR²R³ as a solution in the separated organic phase, and the amine can be used for providing compounds of the formula (II).

The compounds of the general formulae (III) and (V) are suitable for synthesizing a large number of compounds which are of interest as active compounds, such as, for example, for preparing 3-halomethylpyrazol-4-carboxamides, in particular 3-halomethylpyrazol-4-carboxanilides.

Suitable methods for preparing anilides by reacting carboxylic acids or carbonyl esters with aromatic amines are known to the person skilled in the art, for example from the prior art cited at the outset, and also from J. March, Advanced Organic Chemistry, 2nd ed., 382 f, McGraw-Hill, 1977 and Organikum, 21st edition, Wiley-VCH, Weinheim 2001, pp. 481-484 and the literature cited therein.

Examples of 3-halomethylpyrazol-4-carboxamides which can be prepared by this route are:

N-(2-bicyclopropyl-2-ylphenyl)-3-difluoromethyl-1-methylpyrazol-4-ylcarboxamide,
N-(3',4',5'-trifluorobiphenyl-2-yl)-3-fluoromethyl-1-methylpyrazol-4-ylcarboxamide,
N-(3',4',5'-trifluorobiphenyl-2-yl)-3-(chlorofluoromethyl)-1-methylpyrazol-4-ylcarboxamide,
N-(3',4',5'-trifluorobiphenyl-2-yl)-3-difluoromethyl-1-methylpyrazol-4-ylcarboxamide,
N-(3',4',5'-trifluorobiphenyl-2-yl)-3-(chlorodifluoromethyl)-1-methylpyrazol-4-ylcarboxamide
N-(3',4',5'-trifluorobiphenyl-2-yl)-1-methyl-3-trifluoromethylpyrazol-4-ylcarboxamide,
N-(2',4',5'-trifluorobiphenyl-2-yl)-3-fluoromethyl-1-methylpyrazol-4-ylcarboxamide,
N-(2',4',5'-trifluorobiphenyl-2-yl)-3-chlorofluoromethyl)-1-methylpyrazol-4-ylcarboxamide,
N-(2',4',5'-trifluorobiphenyl-2-yl)-3-difluoromethyl-1-methylpyrazol-4-ylcarboxamide,
N-(2',4',5'-trifluorobiphenyl-2-yl)-3-(chlorodifluoromethyl)-1-methylpyrazol-4-ylcarboxamide,
N-(2',4',5'-trifluorobiphenyl-2-yl)-1-methyl-3-trifluoromethylpyrazol-4-ylcarboxamide,
N-(3',4'-dichloro-3-fluorobiphenyl-2-yl)-1-methyl-3-trifluoromethyl-1H-pyrazol-4-ylcarboxamide,
N-(3',4'-dichloro-3-fluorobiphenyl-2-yl)-1-methyl-3-difluoromethyl-1H-pyrazol-4-ylcarboxamide,
N-(3',4'-difluoro-3-fluorobiphenyl-2-yl)-1-methyl-3-trifluoromethyl-1H-pyrazol-4-carboxamide,
N-(3',4'-difluoro-3-fluorobiphenyl-2-yl)-1-methyl-3-difluoromethyl-1H-pyrazol-4-ylcarboxamide,
N-(3'-chloro-4'-fluoro-3-fluorobiphenyl-2-yl)-1-methyl-3-difluoromethyl-1H-pyrazol-4-ylcarboxamide,
N-(3',4'-dichloro-4-fluorobiphenyl-2-yl)-1-methyl-3-difluoromethyl-1H-pyrazol-4-ylcarboxamide,
N-(3',4'-difluoro-4-fluorobiphenyl-2-yl)-1-methyl-3-difluoromethyl-1H-pyrazol-4-ylcarboxamide,
N-(3',4'-dichloro-4-fluorobiphenyl-2-yl)-1-methyl-3-difluoromethyl-1H-pyrazol-4-ylcarboxamide,
N-(3',4'-difluoro-4-fluorobiphenyl-2-yl)-1-methyl-3-difluoromethyl-1H-pyrazol-4-ylcarboxamide,
N-(3'-chloro-4'-fluoro-4-fluorobiphenyl-2-yl)-1-methyl-3-difluoromethyl-1H-pyrazol-4-ylcarboxamide,
N-(3',4'-dichloro-5-fluorobiphenyl-2-yl)-1-methyl-3-trifluoromethyl-1H-pyrazol-4-ylcarboxamide,
N-(3',4'-difluoro-5-fluorobiphenyl-2-yl)-1-methyl-3-trifluoromethyl-1H-pyrazol-4-ylcarboxamide
N-(3',4'-dichloro-5-fluorobiphenyl-2-yl)-1-methyl-3-difluoromethyl-1H-pyrazol-4-ylcarboxamide,
N-(3',4'-difluoro-5-fluorobiphenyl-2-yl)-1-methyl-3-difluoromethyl-1H-pyrazol-4-ylcarboxamide,
N-(3'-chloro-4'-fluoro-5-fluorobiphenyl-2-yl)-1-methyl-3-difluoromethyl-1H-pyrazol-4-ylcarboxamide,
N-(4'-fluoro-4-fluorobiphenyl-2-yl)-1-methyl-3-trifluoromethyl-1H-pyrazol-4-ylcarboxamide,
N-(4'-fluoro-5-fluorobiphenyl-2-yl)-1-methyl-3-trifluoromethyl-1H-pyrazol-4-yl)carboxamide,
N-(4'-chloro-5-fluorobiphenyl-2-yl)-1-methyl-3-trifluoromethyl-1H-pyrazol-4-ylcarboxamide,
N-(4'-methyl-5-fluorobiphenyl-2-yl)-1-methyl-3-trifluoromethyl-1H-pyrazol-4-ylcarboxamide,
N-(4'-fluoro-6-fluorobiphenyl-2-yl)-1-methyl-3-trifluoromethyl-1H-pyrazol-4-ylcarboxamide,
N-[2-(1,1,2,3,3,3-hexafluoropropoxy)phenyl]-3-difluoromethyl-1-methyl-1H-pyrazol-4-ylcarboxamide,
N-[4'-(trifluoromethylthio)biphenyl-2-yl]-3-difluoromethyl-1-methyl-1H-pyrazol-4-ylcarboxamide,
N-[4'-(trifluoromethylthio)-biphenyl-2-yl]-1-methyl-3-trifluoromethyl-1-methyl-1H-pyrazol-4-ylcarboxamide,
3-(difluoromethyl)-1-methyl-N-[1,2,3,4-tetrahydro-9-(1-methylethyl)-1,4-methanonaphthalen-5-yl]-1H-pyrazol-4-ylcarboxamide,
N-(3'-chloro-5-fluorobiphenyl-2-yl)-3-(difluoromethyl)-1-methylpyrazol-4-ylcarboxamide,
N-(4'-chloro-5-fluorobiphenyl-2-yl)-3-(difluoromethyl)-1-methylpyrazol-4-ylcarboxamide,
N-(4'-chlorobiphenyl-2-yl)-3-(difluoromethyl)-1-methylpyrazol-4-ylcarboxamide,
N-(4'-bromobiphenyl-2-yl)-3-(difluoromethyl)-1-methylpyrazol-4-ylcarboxamide,
N-(4'-iodobiphenyl-2-yl)-3-(difluoromethyl)-1-methylpyrazol-4-ylcarboxamide,
N-(3',5'-difluorobiphenyl-2-yl)-3-(difluoromethyl)-1-methylpyrazol-4-ylcarboxamide,
N-(2-chloro-4-fluorophenyl)-3-(difluoromethyl)-1-methylpyrazol-4-ylcarboxamide,
N-(2-bromo-4-fluorophenyl)-3-(difluoromethyl)-1-methylpyrazol-4-ylcarboxamide and
N-(2-iodo-4-fluorophenyl)-3-(difluoromethyl)-1-methylpyrazol-4-ylcarboxamide.

Hereinbelow, the present invention is illustrated in more detail by non-limiting examples.

EXAMPLES

1. Preparation of Compounds of the Formula (I)

Preparation Example I.1

Ethyl 4,4-difluoro-3-oxo-2-(piperidin-1-ylmethylidene)butyrate

Ethyl 3-piperidin-1-ylacrylate (99%, 8.7 g, 50 mmol) and KF (spray dried) (4.44 g, 76.3 mmol) were initially charged in 100 ml of toluene and cooled to −30° C. At this temperature, difluoroacetyl fluoride (98%, 6.10 g, 61 mmol) was then introduced. The reaction mixture was stirred at −30° C. for 3 h and then, over a period of 1 h, warmed to room temperature. The reaction mixture was washed with deionized water (50 ml). After separation of the phases, the aqueous phase was extracted once with toluene (100 ml). The toluene phases were combined and washed with an aqueous saturated NaCl solution (100 ml), and the solvent was then removed under reduced pressure. This gave ethyl 4,4-difluoro-3-oxo-2-(1-piperidin-1-ylmethylidene)butyrate as an orange oil (amount: 13.0 g; purity according to GC: 91.2%; yield: 94%). $^1$H-NMR (CDCl$_3$): δ=1.3 (t, 3H), 1.75 (m, 6H), 3.3 (m, 2H), 3.6 (m, 2H), 4.25 (q, 2H), 6.6 (t, 1H), 7.85 ppm (s, 1H).

Preparation Example I.2

Methyl 4,4,4-trifluoro-3-oxo-2-(piperidin-1-ylmethylidene)butyrate

Methyl 3-piperidin-1-ylacrylate (97%, 25 g, 0.14 mol) and KF (12.5 g, 76.3 mmol) were initially charged in 250 ml of toluene and cooled to −30° C. At this temperature, trifluoroacetyl fluoride (99.5%, 18.3 g, 0.16 mol) was then introduced. The reaction mixture was stirred at −30° C. for 3 h and then, over a period of one hour, warmed to room temperature. The reaction mixture was washed with deionized water (100 ml). After phase separation, the aqueous phase was extracted once with toluene (100 ml). The toluene phases were combined, washed with an aqueous sat. NaCl solution (100 ml) and then freed from the solvent under reduced pressure. Methyl 4,4,4-trifluoro-3-oxo-2-(piperidin-1-ylmethylidene)butyrate was obtained as an orange solid (amount: 38.0 g; purity according to GC: 98%; yield: 98%). $^1$H-NMR (CDCl$_3$): δ=1.75 (m, 6H), 3.3 (m, 2H), 3.6 (m, 2H), 3.75 (s, 3H), 7.65 ppm (s, 1H).

2. Preparation of Compounds of the Formula (III)

Preparation Example III.1

Ethyl 3-difluoromethyl-1-methyl-1H-pyrazol-4-ylcarboxylate (Alternative 1)

Methylhydrazine (0.33 g, 7 mmol) was dissolved in toluene (50 ml) and cooled to −50° C. At this temperature, a solution of ethyl 4,4-difluoro-3-oxo-2-(1-piperidin-1-ylmethylidene)butyrate (85.5%, 2.0 g, 6.5 mmol) in toluene (50 ml) was added dropwise to the reaction mixture. The reaction mixture was stirred at −50° C. for 2 h and then, over a period of 1 hour, warmed to room temperature. Under reduced pressure, the reaction mixture was then freed from the solvent. The residue was dissolved in ethyl acetate (50 ml) and washed with deionized water (50 ml). The organic phase was dried over MgSO$_4$, and the solvent was then removed under reduced pressure. The residue obtained was ethyl 3-difluoromethyl-1-methyl-1H-pyrazol-4-ylcarboxylate (amount: 1.7 g; purity according to GC: 76.3% (based on the 3-isomer); yield: 97%). The isomer ratio of 3-isomer to 5-isomer in the residue was 97:3. $^1$H-NMR (CDCl$_3$): δ=1.35 (t, 3H), 3.95 (s, 2H), 4.3 (q, 2H), 7.12 (t, 1H), 7.9 ppm (s, 1H).

Preparation Example III.2

Ethyl 3-difluoromethyl-1-methyl-1H-pyrazol-4-ylcarboxylate (Alternative 2)

An aqueous solution of methylhydrazine (35%, 0.95 g, 7 mmol) was mixed with toluene (50 ml) and cooled to −50° C. At this temperature, a solution of ethyl 4,4-difluoro-3-oxo-2-(1-piperidin-1-ylmethylidene)butyrate (85.5%, 2.0 g, 6.5 mmol) in toluene (50 ml) was added dropwise to the reaction mixture. The reaction mixture was stirred at −50° C. for 2 h and then, over a period of 1 hour, warmed to room temperature. Under reduced pressure, the reaction mixture was then freed from the solvent. The residue was dissolved in ethyl acetate (50 ml) and washed with deionized water (50 ml). The organic phase was dried over MgSO$_4$, and the solvent was then removed under reduced pressure. The residue obtained was ethyl 3-difluoromethyl-1-methyl-1H-pyrazol-4-ylcarboxylate (amount: 1.7 g; purity according to GC: 59.3% (based on the 3-isomer); yield: 75.4%). The isomer ratio of 3-isomer to 5-isomer in the residue was 76:24.

Preparation Example III.3

Ethyl 3-difluoromethyl-1-methyl-1H-pyrazol-4-ylcarboxylate (Alternative 3)

An aqueous solution of methylhydrazine (35%, 0.95 g, 7 mmol) was mixed with triethylamine (0.66 g, 6.5 mol) and toluene (50 ml) and cooled to −50° C. At this temperature, a solution of ethyl 4,4-difluoro-3-oxo-2-(1-piperidin-1-ylmethylidene)-butyrate (85.5%, 2.0 g, 6.5 mmol) in toluene (50 ml) was added dropwise. The reaction mixture was stirred at −50° C. for 2 h and then, over a period of 1 hour, warmed to room temperature. Under reduced pressure, the reaction mixture was then freed from the solvent. The residue was dissolved in ethyl acetate (50 ml) and washed with deionized water (50 ml). The organic phase was dried over MgSO$_4$, and the solvent was then removed under reduced pressure. The residue obtained was ethyl 3-difluoromethyl-1-methyl-1H-pyrazol-4-ylcarboxylate (amount: 1.8 g; purity according to GC: 64.5% (based on the 3-isomer); yield: 73.4%). The isomer ratio of 3-isomer to 5-isomer in the residue was 84:16.

Preparation Example III.4

Ethyl 3-difluoromethyl-1-methyl-1H-pyrazol-4-ylcarboxylate (Alternative 4)

An aqueous solution of methylhydrazine (35%, 0.95 g, 7 mmol) was mixed with molecular sieve (5.0 g) and toluene (50 ml) and cooled to −50° C. At this temperature, a solution of ethyl 4,4-difluoro-3-oxo-2-(1-piperidin-1-ylmethylidene) butyrate (85.5%, 2.0 g, 6.5 mmol) in toluene (50 ml) was added dropwise. The reaction mixture was stirred at −50° C. for 2 h and then, over a period of 1 hour, warmed to room temperature. The reaction mixture was then filtered and freed from the solvent under reduced pressure. The residue was dissolved in ethyl acetate (50 ml) and washed with deionized water (50 ml). The organic phase was dried over MgSO$_4$, and the solvent was then removed under reduced pressure. The residue obtained was ethyl 3-difluoromethyl-1-methyl-1H-pyrazol-4-ylcarboxylate (amount: 1.3 g; purity according to GC: 72.9% (based on the 3-isomer); yield: 71.0%). The isomer ratio of 3-isomer to 5-isomer in the residue was 88:12.

Preparation Example III.5

Ethyl 3-difluoromethyl-1-methyl-1H-pyrazol-4-ylcarboxylate (Alternative 5)

An aqueous solution of methylhydrazine (35%, 1.03 g, 8 mmol) was mixed with aqueous sodium hydroxide solution (10%, 2.6 g, 6.5 mmol) and ethanol (50 ml) and cooled to −3° C. At this temperature, a solution of ethyl 4,4-difluoro-3-oxo-2-(1-piperidin-1-ylmethylidene)butyrate (85.5%, 2.0 g, 6.5 mmol) in toluene (50 ml) was added dropwise. The reaction mixture was stirred at −3° C. for 2 h and then, over a period of 1 hour, warmed to room temperature. Under reduced pressure, the reaction mixture was then freed from the solvent. The residue was dissolved in ethyl acetate (50 ml) and washed with deionized water (50 ml). The organic phase was dried over MgSO$_4$, and the solvent was then removed under reduced pressure. The residue obtained was ethyl 3-difluoromethyl-1-methyl-1H-pyrazol-4-ylcarboxylate (amount:

1.0 g; purity according to GC: 80.6% (based on the 3-isomer); yield: 66.3%). The isomer ratio of 3-isomer to 5-isomer in the residue was 98:2.

3. Preparation of Compounds of the Formula (V)

Preparation Example V.1

3-difluoromethyl-1-methyl-1H-pyrazol-4-ylcarboxylic acid

A mixture of ethyl 3-difluoromethyl-1-methyl-1H-pyrazol-4-ylcarboxylate (1.4 g, 52 mmol) and aqueous sodium hydroxide solution (10% strength, 3.1 g, 8 mmol) was stirred at 60° C. for 2 h. The reaction mixture was cooled to room temperature, and the pH was then adjusted to 1 using concentrated hydrochloric acid. The reaction mixture was cooled further to 0° C., resulting in the precipitation of a solid. The precipitated solid was filtered off, washed with cyclohexane and dried under reduced pressure. This gave 3-difluoromethyl-1-methyl-1H-pyrazol-4-ylcarboxylic acid as a solid (amount: 0.8 g; yield: 87%). $^1$H-NMR (DMSO-$d_6$): δ=3.9 (s, 2H), 7.2 (t, 1H), 8.35 ppm (s, 1H).

Preparation Example V.2

3-difluoromethyl-1-methyl-1H-pyrazol-4-ylcarboxylic acid (one-pot reaction)

At −30° C., difluoroacetyl fluoride (37.3 g, 0.373 mol; 98%) was introduced into a solution of methyl 3-piperidin-1-ylacrylate (99%, 58.1 g, 0.34 mol) and KF (spray dried) (29.6 g, 0.51 mol) in toluene (500 ml). The reaction mixture was stirred at −30° C. for 3 h and then, over a period of 1 hour, warmed to room temperature. The reaction mixture was washed with deionized water (400 ml). After separation of the phases, the aqueous phase was extracted once with toluene (200 ml). The toluene phases were combined and, under reduced pressure, concentrated to about 600 ml. The reaction solution obtained in this manner was, at −50° C., added dropwise to a solution of methylhydrazine (17.57 g, 0.373 mol) in toluene (150 ml). The reaction mixture was stirred at −50° C. for 2 h and then, over a period of 1 hour, warmed to room temperature. Aqueous sodium hydroxide solution (10%, 210.7 g, 0.527 mol) was then added, and the reaction mixture was heated under reflux conditions for 2 h. After cooling to room temperature, the phases were separated. The toluene phase was extracted with aqueous sodium hydroxide solution (10% strength, 100 ml). The aqueous phases were combined, adjusted to a pH of 1 using hydrochloric acid (conc.) and cooled to 0° C. The precipitated solid was filtered off, washed with cyclohexane and dried at 60° C. under reduced pressure. This gave 3-difluoromethyl-1-methyl-1H-pyrazol-4-ylcarboxylic acid in an amount of 56.3 g in a purity of 89% (according to quant. HPLC) (yield: 0.285 mol, 85%). By extracting the filtrate with ethyl acetate, a further 3.5 g of a solid were obtained which, according to quant. HPLC, consisted to 30% of 3-difluoromethyl-1-methyl-1H-pyrazol-4-ylcarboxylic acid. $^1$H-NMR (CDCl$_3$): δ=3.85 (s, 2H), 3.95 (s, 3H), 7.12 (t, 1H), 7.9 ppm (s, 1H).

Preparation Example V.3

3-difluoromethyl-1-methyl-1H-pyrazol-4-ylcarboxylic acid (One-Pot Reaction)

At −30° C., difluoroacetyl fluoride (18.7 g, 0.187 mol; 98%) was introduced into a solution of methyl 3-piperidin-1-ylacrylate (99%, 29.0 g, 0.17 mol) and KF (technical grade) (10.7 g, 0.25 mol) in toluene (250 ml). The reaction mixture was stirred at −30° C. for 3 h. The mixture was then, over a period of one hour, warmed to room temperature. The reaction mixture was washed with deionized water (200 ml). After separation of the phases, the aqueous phase was extracted once with toluene (100 ml). The toluene phases were combined and, under reduced pressure, concentrated to about 300 ml. At −50° C., the reaction solution obtained in this manner was added dropwise to a solution of methylhydrazine (8.79 g, 0.187 mol) in toluene (100 ml). The reaction mixture was stirred at −50° C. for 2 h and then, over a period of one hour, warmed to room temperature. Aqueous sodium hydroxide solution (10% strength, 105.3 g, 0.263 mol) was then added to the reaction mixture, and the mixture was heated under reflux conditions for 2 h. After cooling to room temperature, the phases were separated. The toluene phase was extracted with aqueous sodium hydroxide solution (10% strength, 100 ml). The aqueous phases were combined, adjusted to pH 1 using hydrochloric acid (conc.) and cooled to 0° C. The precipitated solid was filtered off, washed with cyclohexane and dried at 60° C. under reduced pressure. 3-Difluoromethyl-1-methyl-1H-pyrazol-4-ylcarboxylic acid was obtained in an amount of 29.1 g in a purity of 89.4% (according to quant. HPLC) (yield: 88%). Extraction of the filtrate with ethyl acetate gave a further 1.4 g of a solid which, according to quant. HPLC, consisted to 36% of 3-difluoromethyl-1-methyl-1H-pyrazol-4-ylcarboxylic acid.

Preparation Example V.4

3-difluoromethyl-1-methyl-1H-pyrazol-4-ylcarboxylic acid (one-pot reaction; NaF, technical grade)

The experiment was carried out analogously to the previous example, but in the presence of NaF as HF scavenger.

3-Difluoromethyl-1-methyl-1H-pyrazol-4-ylcarboxylic acid was obtained in an amount of 27.5 g in a purity of 91.6% (according to quant. HPLC) (yield: 86%). Extraction of the filtrate with ethyl acetate gave a further 1.7 g of a solid which, according to quant. HPLC, consisted of 40% of 3-difluoromethyl-1-methyl-1H-pyrazol-4-ylcarboxylic acid.

Preparation Example V.5

3-difluoromethyl-1-methyl-1H-pyrazol-4-ylcarboxylic acid (one-pot reaction; methylhydrazine, aqueous)

The experiment was carried out analogously to example V.3, but in the presence of aqueous 35% strength methylhydrazine.

3-Difluoromethyl-1-methyl-1H-pyrazol-4-ylcarboxylic acid was obtained in an amount of 24.1 g in a purity of 70.8% (according to quant. HPLC) (yield: 61%). Extraction of the filtrate with ethyl acetate gave a further 5.3 g of a solid which, according to quant. HPLC, consisted to 21% of 3-difluoromethyl-1-methyl-1H-pyrazol-4-ylcarboxylic acid.

Preparation Example V.6

3-trifluoromethyl-1-methyl-1H-pyrazol-4-ylcarboxylic acid (One-Pot Reaction)

At −30° C., trifluoroacetyl fluoride (18.3 g, 0.16 mol; 99.5%) was introduced into a solution of methyl 3-piperidin-1-ylacrylate (97%, 25 g, 0.14 mol) and KF (12.5 g, 0.51 mol)

in toluene (250 ml). The reaction mixture was stirred at −30° C. for 3 h and then, over a period of one hour, warmed to room temperature. The reaction mixture was washed with deionized water (400 ml). After phase separation, the aqueous phase was extracted once with toluene (200 ml). The toluene phases were combined and, under reduced pressure, concentrated to about 600 ml. The reaction solution obtained in this manner was, at −50° C., added dropwise to a solution of methylhydrazine (7.4 g, 0.16 mol) in toluene (150 ml). The reaction mixture was stirred at −50° C. for 2 h and then, over a period of one hour, warmed to room temperature. Aqueous sodium hydroxide solution (10% strength, 69.4 g, 0.17 mol) was then added, and the reaction mixture was heated under reflux conditions for 2 h. After cooling to room temperature, the phases were separated. The toluene phase was extracted with aqueous sodium hydroxide solution (10% strength, 100 ml). The aqueous phases were combined, adjusted to pH 1 using hydrochloric acid (conc.) and cooled to 0° C. The precipitated solid was filtered off, washed with cyclohexane and, at 60° C., dried under reduced pressure. 3-trifluoromethyl-1-methyl-1H-pyrazol-4-ylcarboxylic acid was obtained in an amount of 21.8 g and a purity of 98% (according to $^1$H-NMR) (yield: 0.12 mol, 81%).

$^1$H-NMR (CDCl$_3$): δ=3.95 (s, 3H), 8.45 ppm (s, 1H).

The invention claimed is:

1. A process for preparing compounds of the formula (I)

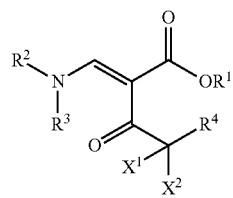

(I)

wherein

R$^1$ is C$_1$-C$_6$-alkyl, C$_1$-C$_6$-haloalkyl, C$_2$-C$_6$-alkenyl, C$_3$-C$_{10}$-cycloalkyl or benzyl, where the two last mentioned radicals are unsubstituted or have 1, 2 or 3 substituents independently of one another selected from the group consisting of halogen, CN, nitro, C$_1$-C$_4$-alkyl, C$_1$-C$_4$-haloalkyl, C$_1$-C$_4$-alkoxy and C$_1$-C$_4$-haloalkoxy;

R$^2$ and R$^3$ independently of one another are C$_1$-C$_6$-alkyl, C$_1$-C$_6$-haloalkyl, C$_2$-C$_6$-alkenyl, C$_3$-C$_{10}$-cycloalkyl or benzyl, where the two last mentioned radicals are unsubstituted or have 1, 2 or 3 substituents independently of one another selected from the group consisting of halogen, CN, nitro, C$_1$-C$_4$-alkyl, C$_1$-C$_4$-haloalkyl, C$_1$-C$_4$-alkoxy and C$_1$-C$_4$-haloalkoxy; or R$^2$ together with R$^3$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members;

R$^4$ is hydrogen, fluorine or chlorine; and

X$^1$ and X$^2$ independently of one another are fluorine or chlorine;

comprising reacting a compound of the formula (II)

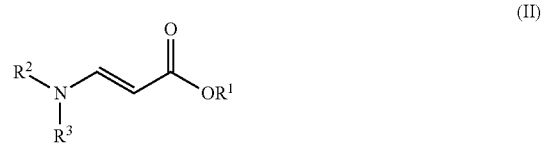

(II)

with a compound of the formula X$^1$X$^2$R$^4$C—C(═O)—F in the presence of at least one alkali or alkaline earth metal fluoride.

2. The process of claim 1, wherein the compound of the formula (II) is reacted with the compound of the formula X$^1$X$^2$R$^4$—C—C(═O)—F in the presence of at least equimolar amounts of at least one alkali or alkaline earth metal fluoride, based on the compound of the formula (II).

3. The process of claim 1, wherein the compound of the formula (II) is reacted with the compound of the formula X$^1$X$^2$R$^4$C—C(═O)—F in the presence of potassium fluoride.

4. The process of claim 1, wherein the compound of the formula (II) is reacted with a compound of the formula X$^1$X$^2$R$^4$C—C(═O)—F in which R$^4$ is hydrogen or fluorine.

5. The process of claim 1, wherein the compound of the formula (II) is reacted with a compound of the formula X$^1$X$^2$R$^4$C—C(═O)—F, in which X$^1$ and X$^2$ are each fluorine.

6. The process according to claim 1, wherein the compound of the formula (II) is reacted with difluoroacetyl fluoride.

7. The process of claim 1, wherein the reaction of the compound of the formula (II) with the compound of the formula X$^1$X$^2$R$^4$C—C(═O)—F is carried out essentially anhydrously.

8. The process of claim 1, wherein R$^2$ and R$^3$ in the compounds of the formulae (I) and (II) together with the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members.

9. The process of claim 8, wherein NR$^2$R$^3$ is a saturated optionally substituted, 5- or 6-membered heterocyclic radical which, in addition to the nitrogen atom, may contain a further heteroatom selected from the group consisting of O, N and S as ring member.

10. The process of claim 9, wherein NR$^2$R$^3$ is pyrrolidin-1-yl, oxazolidin-3-yl, 3-methylimidazolin-1-yl, piperidin-1-yl, morpholin-4-yl or 4-methylpiperazin-1-yl.

11. A process for preparing halomethyl-substituted pyrazol-4-ylcarboxylic esters of the formula (III)

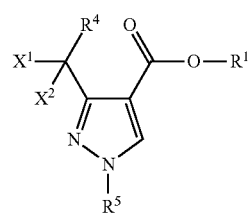

(III)

wherein

R$^1$ is C$_1$-C$_6$-alkyl, C$_1$-C$_6$-haloalkyl, C$_2$-C$_6$-alkenyl, C$_3$-C$_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
$R^4$ is hydrogen, fluorine or chlorine;
$R^5$ is hydrogen, $C_1$-$C_6$-alkyl, $C_1$-$C_6$-haloalkyl, $C_3$-$C_{10}$-cycloalkyl, phenyl or benzyl where the three last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; and
$X^1$ and $X^2$ are independently of one another fluorine or chlorine;
comprising
a) providing a compound of the formula (I),

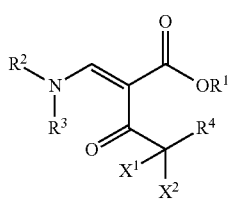

(I)

wherein
$R^2$ and $R^3$ independently of one another are $C_1$-$C_6$-alkyl, $C_1$-$C_6$-haloalkyl, $C_2$-$C_6$-alkenyl, $C_3$-$C_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; or
$R^2$ together with $R^3$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members;
and $R^1$, $X^1$, and $X^2$ are as defined above;
b) and reacting the compound of the formula (I) with a hydrazine compound of the formula (IV)

(IV)

wherein said providing a compound of formula (I) comprises reacting a compound of the formula (II)

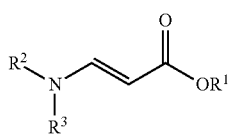

(II)

with a compound of the formula $X^1X^2R^4C-C(=O)-F$ in the presence of at least one alkali or alkaline earth metal fluoride.

12. The process of claim 11, wherein $R^5$ in the compounds of the formulae (III) and (IV) is $C_1$-$C_4$-alkyl.

13. The process of claim 11, wherein the compound of the formula (I) is provided in the form of a reaction mixture without prior isolation of the compound of the formula (I).

14. A process for preparing a pyrazol-4-carboxylic acid of the formula (V)

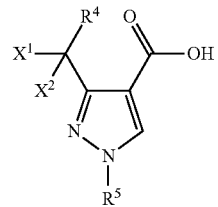

(V)

wherein
$R^4$ is hydrogen, fluorine or chlorine;
$R^5$ is hydrogen, $C_1$-$C_6$-alkyl, $C_1$-$C_6$-haloalkyl, $C_3$-$C_{10}$-cycloalkyl, phenyl or benzyl where the three last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; and
$X^1$ and $X^2$ are independently of one another fluorine or chlorine;
comprising providing a compound of the formula (III) and hydrolyzing the compound of the formula (III);
wherein said providing a compound of formula (III) comprises providing a compound of the formula (I),

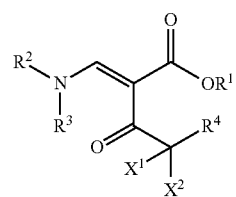

(I)

wherein
$R^1$ is $C_1$-$C_6$-alkyl, $C_1$-$C_6$-haloalkyl, $C_2$-$C_6$-alkenyl, $C_3$-$C_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
$R^2$ and $R^3$ independently of one another are $C_1$-$C_6$-alkyl, $C_1$-$C_6$-haloalkyl, $C_2$-$C_6$-alkenyl, $C_3$-$C_{10}$-cycloalkyl or benzyl, where the two last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; or
$R^2$ together with $R^3$ and the nitrogen atom to which the two radicals are attached are an optionally substituted 5- to 10-membered heterocyclic radical which, in addition to the nitrogen atom, may contain a further 1, 2 or 3 heteroatoms selected from the group consisting of O, N and S as ring members;
and $R^4$, $X^1$, and $X^2$ are as defined above; and
b) reacting the compound of the formula (I) with a hydrazine compound of the formula (IV)

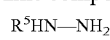

(IV)

wherein
$R^5$ is hydrogen, $C_1$-$C_6$-alkyl, $C_1$-$C_6$-haloalkyl, $C_3$-$C_{10}$-cycloalkyl, phenyl or benzyl where the three last mentioned radicals are unsubstituted or have 1, 2 or 3 substituents independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
to obtain a compound of formula (III);
and wherein said providing a compound of formula (I) comprises reacting a compound of the formula (II)

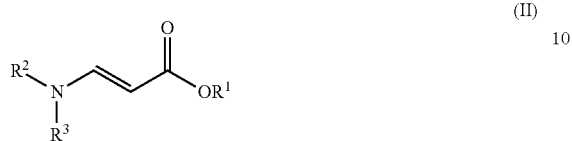

(II)

with a compound of the formula $X^1X^2R^4C\text{—}C(\!=\!O)\text{—}F$ in the presence of at least one alkali or alkaline earth metal fluoride.

15. The process of claim 14, wherein the compound of the formula (III) is hydrolyzed in the form of a reaction mixture without prior isolation of the compound of the formula (III).

16. The process of claim 14, wherein the hydrolysis is carried out in the presence of an aqueous alkali metal hydroxide solution or alkaline earth metal hydroxide solution.

* * * * *